United States Patent [19]

Bradford

[11] Patent Number: Plant 5,666

[45] Date of Patent: Feb. 18, 1986

[54] NECTARINE TREE (KISM GRAND)

[76] Inventor: Norman G. Bradford, 11875 E. Savana Rd., Le Grand, Calif. 95333

[21] Appl. No.: 622,091

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

*Attorney, Agent, or Firm*—Vergil L. Gerard

[57] ABSTRACT

The present invention relates to a nectarine tree and more particularly to a new and distinct variety broadly characterized by a medium size, vigorous, hardy, very productive and regular bearing tree, the fruit of which ripens about five days earlier than the Late LeGrand variety (U.S. Plant Pat. No. 1,038) under the ecological conditions described. The fruit is a clingstone of good eating quality with abundant, rich juice and is of good keeping and shipping quality. The fruit is of large size and attractive, globose form, and has a waxy skin with good red color at picking.

1 Drawing Figure

BACKGROUND OF THE VARIETY

The instant variety of nectarine tree was discovered by me on my farms in Merced County (San Joaquin Valley), Calif., as a seedling of a cross of Red Free (U.S. Plant Pat. No. 3,385) nectarine, which was pollinated by Sparkling Red (U.S. Plant Pat. No. 4,314). The instand variety was selected for asexual reproduction because it demonstrated good commercial characteristics and because of its ripening date, which is five days before Late LeGrand (U.S. Plant Pat. No. 1,035), and is a further improvement on that variety in having fruit with smoother surface which is redder in color at picking time, has a better eating quality, is of large size, attractive, globose shape, and is distinguished by a sweet kernel. Also, the tree is more vigorous than the Late LeGrand.

As to the parent plants, the instant variety resembles Tom Grand in that they are both clingstone and similar in size and eating quality, but differs distinctly because the instant variety ripens about 20 days earlier and has a much redder color. The instant variety differs from Red Free in being a clingstone instead of a freestone and of larger size, and ripening about eight days later. It differs from Sparkling Red in being a clingstone instead of a freestone, and being less acidic and of larger size. I have compared the instant variety to Late LeGrand because of ripening time proximity, which makes it a market competitor to that variety.

The instant variety was propagated by me at the same location where it was discovered by asexually reproducing by budding and grafting, and such reproduction of plant and fruit characteristics were true to the original plant in all respects.

DRAWINGS

The accompanying photograph shows the characteristics of the whole fruit in skin color and form, a characteristic fruit divided on its suture plane showing the flesh and stone cavity, and a characteristic stone, and leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the stage of being slightly under ripe and hard in the 1983 growing season. All color plate identifications are by reference to Dictionary of Color 1950 (2d ed) by Maerz and Paul.

TREE

General: Hardy, vigorous, spreading and dense, of medium size and vase formed. Very productive and regular bearing.

Trunk: Medium size, medium shaggy, numerous lenticels $\frac{1}{4}''$ in length, resembling Soapstone (15 A-7) in color. Bark resembles Acorn (15 F-7) in color.

Branches: Stocky, medium shaggy, brown; dorsal side resembling Burnt Umber (15 12-A), ventral side resembling (15 E-12). Numerous small lenticles.

Leaves: Medium size; length $4\frac{1}{2}''$; elliptical, medium thick, smooth. Apex acuminate. Dorsal side dark green resembling 21-I-6, ventral side lighter green resembling 21 I-2. Base, acute; pinnately net veined; crenate margin; petiole size $\frac{1}{2}''$ long. Glands average two in number, oppositely disposed, medium size, reniform, green. Positioned on petiole or base of blade. A few stipules $\frac{1}{8}''$ in length.

Flower buds: Hardy, medium size, medium length; obtuse, plump, free and pubescent.

Flowers: Medium blooming date compared with other varieties. Large, pink.

Fruit: Maturity when described, slightly under ripe, hard; Aug. 5, 1982.

*Size.*—Uniform, large; axial diameter $2\frac{1}{2}''$, traverse in suture plane, $2\frac{1}{2}''$.

*Form.*—Uniform, symmetrical, globose traverse the diameter.

*Suture.*—An inconspicuous shallow line extending from base to beyond apex. Has slight depression beyond pistil point.

*Ventral surface.*—Strongly rounded, lipped very slightly toward apex with equal lips.

*Cavity.*—Rounded but elongated in suture plane with suture showing on both sides; depth $\frac{1}{2}''$, breadth $\frac{3}{4}''$.

*Base.*—Rounded.

*Apex.*—Short, depressed; oblique pistil point of negligible size.

*Stem.*—Medium size, length $\frac{3}{8}''$, width 3/16".

*Skin.*—Medium thickness, medium texture. Tenacious to flesh. Only slight tendency to crack. Color, red blush resembling Chalet Red (6 K-10) over a yellow under skin.

*Flesh.*—Color: Yellow resembling Snowshoe (10 K-7) streaked with red next to stone. Juice, abundant and rich. Texture, Medium, melting. Fibres, abundant, fine and tender. Ripens evenly. Mild flavor, slight aroma. Good eating quality.

*Stone.*—Clingstone. Elliptical form, acute base, narrow hilum. Apex is mucronate with flattened, equal sides. Surface is irregularly furrowed and pitted throughout. Ridges rounded. Color resembles Coffee (15 A-11). 3/16" thickness of pit wall. Only slight tendency to split. Kernel: oval form, sweet, viable; width 9/16".

*Use.*—Market, long distance shipping. Keeping and shipping quality average. No unusual susceptibilities noted.

I claim:

1. A new and distinct variety of clingstone nectarine tree, substantially as illustrated and described, which most nearly resembles the Late Le Grand nectarine (U.S. Plant Pat. No. 1,035) but is distinguishable therefrom and an improvement thereon in that the tree is more vigorous and its fruit ripens around five days earlier, has a smooth surface substantially free of russets, a redder color when picking ripe, and a better eating quality.

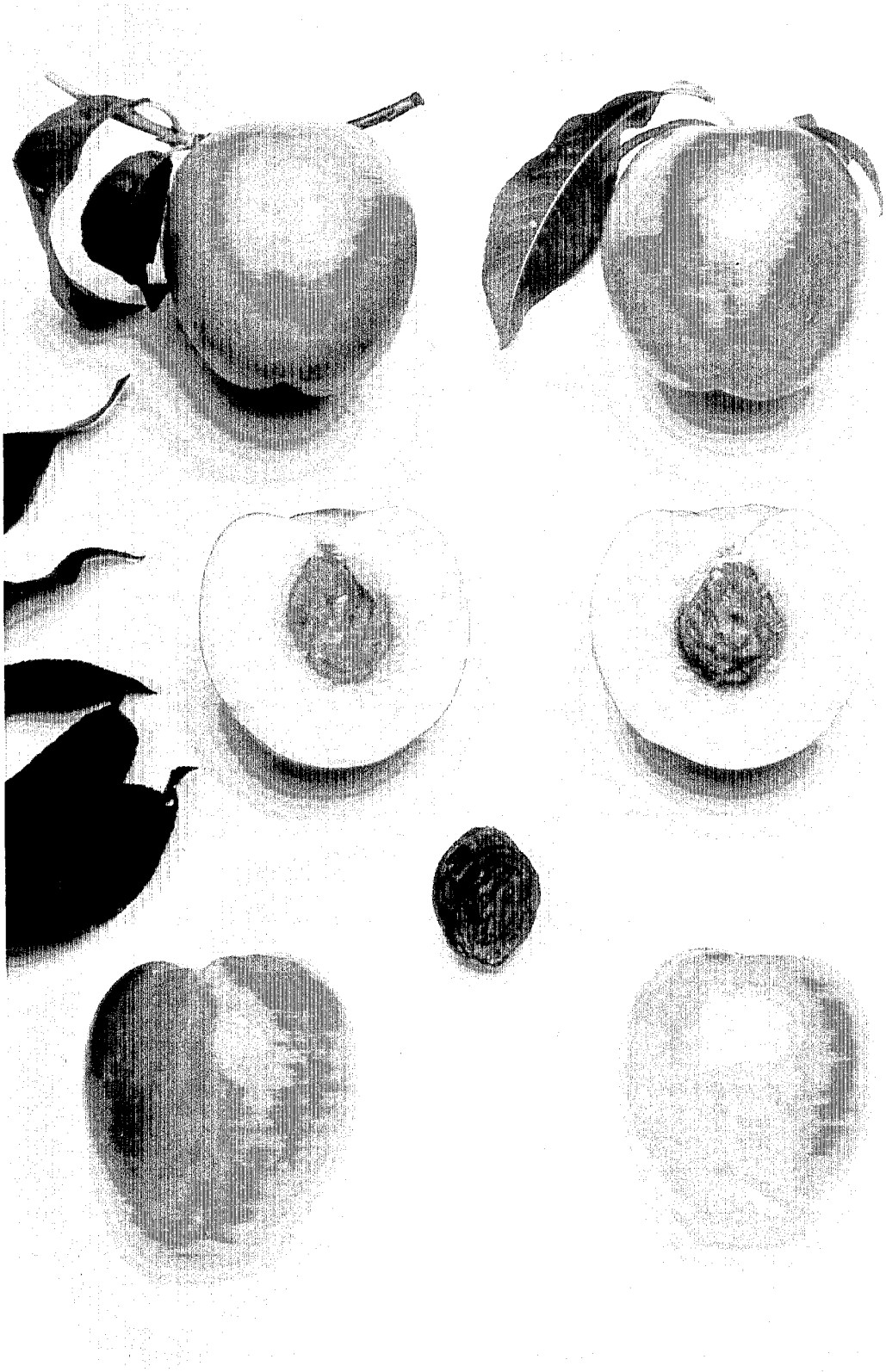

* * * * *